United States Patent [19]
Levin

[11] Patent Number: 5,609,599
[45] Date of Patent: Mar. 11, 1997

[54] LEAK CLIP

[76] Inventor: John M. Levin, 412 Fairview Rd., Narbeth, Pa. 19072

[21] Appl. No.: 508,323
[22] Filed: Jul. 27, 1995
[51] Int. Cl.⁶ .................................................. A61B 17/08
[52] U.S. Cl. ..................... 606/153; 606/151; 606/157; 606/207
[58] Field of Search ..................... 606/151, 157, 606/158, 205, 206, 207, 153; 128/751

[56] References Cited

U.S. PATENT DOCUMENTS 3,091,828  8/1961  Soltis ........................................ 606/151
3,404,677  10/1968  Springer .................................... 606/206
3,840,003  10/1974  Komiya ..................................... 606/151
5,509,922  4/1996  Aranyi et al. ............................ 606/205

*Primary Examiner*—Michael Powell Buiz
*Assistant Examiner*—Mark S. Leonardo
*Attorney, Agent, or Firm*—Caesar, Rivise, Bernstein, Bernstein, Cohen & Pokotilow, Ltd.

[57] ABSTRACT

A leak clip that can be applied through a trocar to immediately close off the entire opening in an internal organ, thereby preventing the leakage of contaminating fluids in the surrounding tissue.

35 Claims, 5 Drawing Sheets

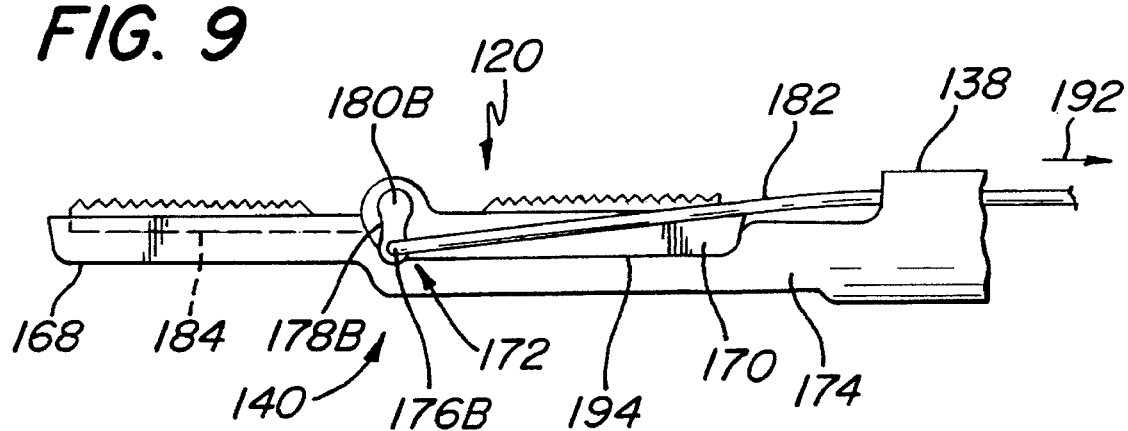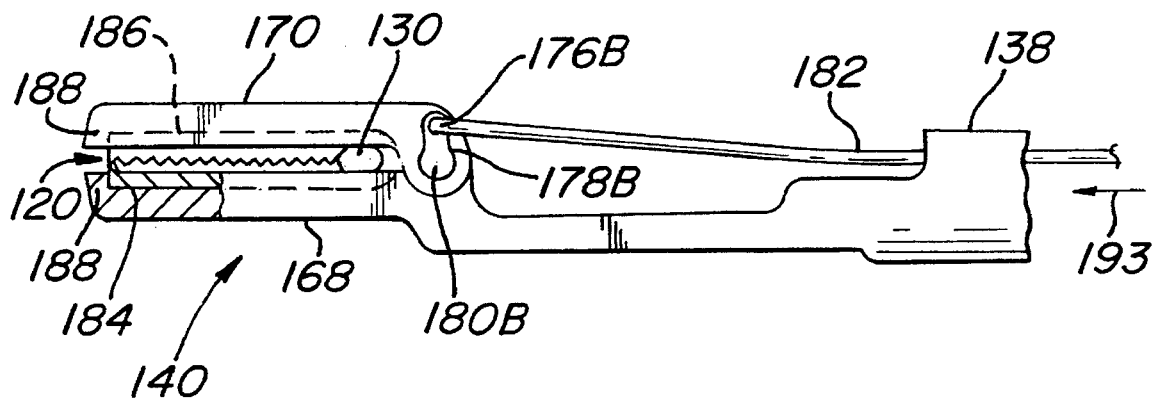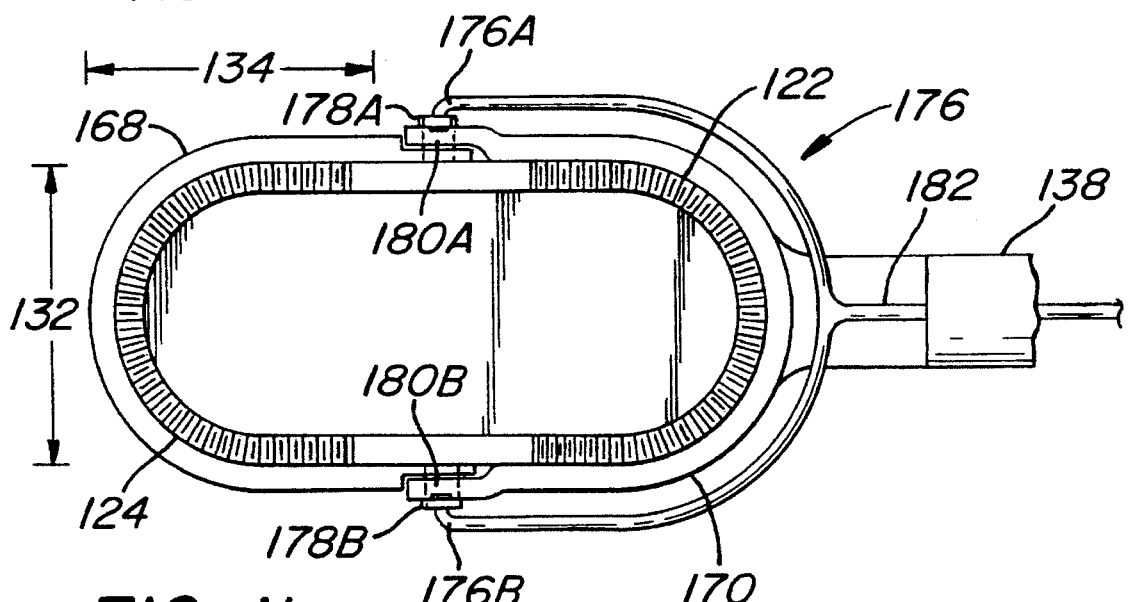

LEAK CLIP

FIELD OF THE INVENTION

This invention relates generally to the field of medical devices, more particularly, to leak clips that can be used during laparoscopic surgery for entirely closing off an opening in an internal organ from leaking, thereby preventing contamination to the surrounding area.

BACKGROUND OF THE INVENTION

The immediate closure of a ruptured organ is presently accomplished by the surgeon applying a standard surgical clamp over the opening or puncture a ruptured organ (e.g., rupture of the gallbladder, bowel/stomach or large blood vessels due to a gunshot wound) once the patient has arrived in the hospital. Typically, such a surgical clamp only pinches the opening but does not entirely close off the opening and as such does not adequately prevent the leakage of any internal fluids (or any viscous but leakable substance) that may contaminate the surrounding organs. The alternative is for the surgeon to suture the opening or puncture closed, but that is time consuming and does not prevent the leakage of fluid in time.

The following U.S. Patents describe various types of surgical clamps: U.S. Pat. No. 5,304,183 (Gourlay et al.); U.S. Pat. No. 4,976,722 (Failla); U.S. Pat. No. 4,856,518 (McFadden); U.S. Pat. No. 4,635,634 (Santos); U.S. Pat. No. 4,586,503 (Kirsch et al.); U.S. Pat. No. 4,519,392 (Lingua); U.S. Pat. No. 4,217,902 (March); U.S. Pat. No. 4,064,881 (Meredith).

The apparatus disclosed by Gourlay et al. is a laparoscopic spring-biased, elongated clamp inserted through a trocar. An applicator applies the clamp and releases and removes the clamp. The clamp includes interdigitating teeth (sawtooth) for clamping the tissue or organ and is used for manipulating/positioning tissue during laparoscopic surgery.

The apparatus disclosed by Failla is a surgical hemostatic clip for providing positive hemostasis of a blood vessel by way of a gapless closure. The clip comprises opposing legs that are hinged with the opposing surfaces having tongue/groove couplings.

The apparatus disclosed by McFadden discloses a laparoscopic clamp with an applicator for opening and closing the clamp which is levered and provides rotation for the clamp application portion.

The apparatus disclosed by Santos is a surgical clip applicator system for receiving a clip and for compressively applying the clip to a body vessel or tissue.

The apparatus disclosed by Kirsch et al. is a surgical microclip used for microvascular anastomoses.

The apparatus by Lingua provides a clamp with teeth, serrations or other interlocking designs for strengthening ocular muscles or occluding blood vessels.

The apparatus disclosed by March is disclosed a clamp which closes the sides of a wound to prevent bleeding. A pair of pliers is used to apply and remove the clamp.

The apparatus disclosed by Meredith discloses an abdominal clip and applicator with upper and lower teeth spaced apart.

However, it is believed that a need exists for a leak clip, to be used in laparoscopic surgery, that permits the entire opening of a ruptured organ to be grasped and closed-off immediately upon application by providing a circumferential seal around the leaking hole.

OBJECTS OF THE INVENTION

Accordingly, it is the general object of this invention to provide an apparatus and a method of use which addresses the aforementioned needs.

It is a further object of this invention to provide an apparatus that clamps shut the entire opening or puncture of a leaking internal organ thereby preventing the contamination of the surrounding area.

It is still a further object of this invention to provide a clamping apparatus that can be used during laparoscopic surgery to entirely clamp shut a leaking internal organ.

It is yet another object of this invention to provide a plurality of applicator heads, for use on conventional laparoscopic applicators, for applying the clamping apparatus using a variety of clamp-opening sizes.

SUMMARY OF THE INVENTION

These and other objects of the instant invention are achieved by providing an apparatus for quickly closing an opening in an internal body part (e.g., gallbladder, common bile duct, bowel/stomach, large blood vessels) to prevent the leakage of contaminating fluids from the opening. The apparatus comprises a clamp having a pair of movable jaws that are pivotally coupled. Each of the jaws has a width of a sufficient dimension to encompass the entire opening whenever the jaws are brought into contact with each other. In addition, each of the jaws has a periphery containing teeth and wherein the respective teeth interdigitate whenever the jaws are brought into contact with each other. Finally, the apparatus further comprises a means for applying the clamp to the opening with the clamp being releasably secured within the means for applying and wherein the means for applying is insertable through a trocar.

In a preferred embodiment, each of the jaws comprises a semi-circular contour and each of the jaws are pivotally joined to each other along the straight edge of each semi-circle and with the jaws being pre-disposed at a predetermined angular orientation.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 9 is side elevation view of the second embodiment of the leak clip installed in an open position within another single-movable jaw applicator;

FIG. 10 is side elevation view of the second embodiment of the leak clip of FIG. 9 in a closed position;

FIG. 11 is top plan view of FIG. 9;

DESCRIPTION OF THE PREFERRED EMBODIMENT OF THE INVENTION

Figure 1:
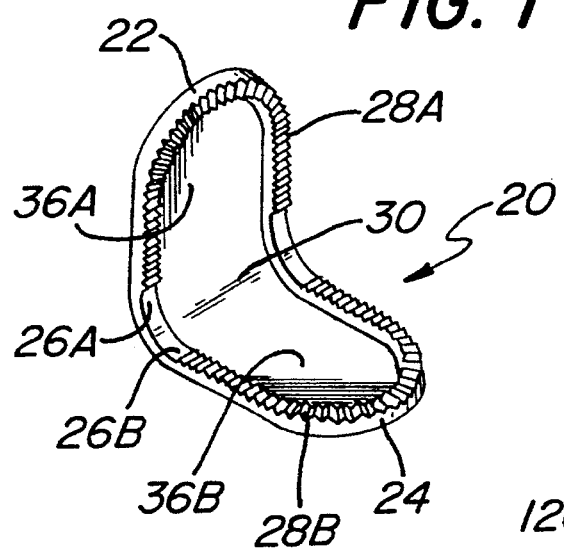
FIG. 1 is an isometric view of a first embodiment of the leak clip.

Referring now in greater detail to the various figures of the drawing wherein like reference characters refer to like parts, a leak clip constructed in accordance with the present invention is shown generally at 20 in FIG. 1. The leak clip 20 comprises an upper jaw 22 and a lower jaw 24 each having opposing outer peripheries 26A and 26B that contain upper teeth 28A and lower teeth 28B. The leak clip 20 is preferably a unitary member that is bent in an "L-shape" to form the upper jaw 22 and the lower jaw 24. The bend acts as a hinge 30 for the upper jaw 22 and lower jaw 24. The leak clip 20 comprises a material that permits the hinge 30 to maintain the jaws 22 and 24 in a closed position (FIGS. 4 and 7) when these jaws 22 and 24 are brought together by a leak clip applicator, to be discussed later.

Figure 5:
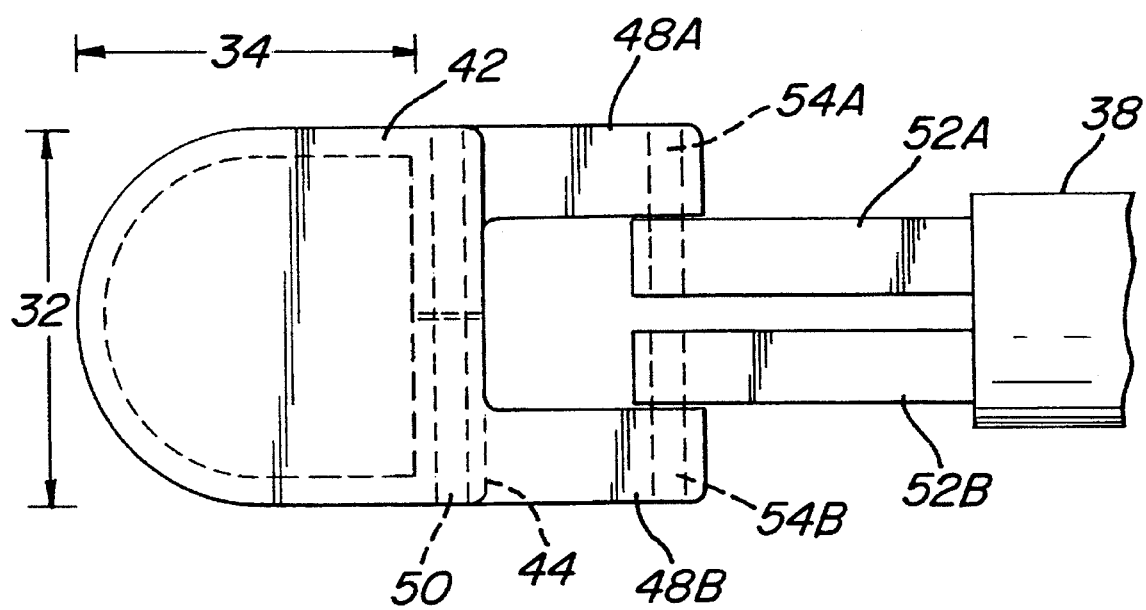
FIG. 5 is a top plan view of FIG. 4.
Figure 13:
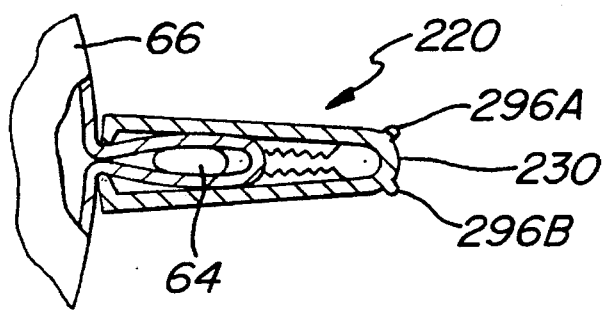
FIG. 13 is a view showing the leak clip totally encompassing the puncture or opening.

The shape of the upper jaw 22 and lower jaw 24 are identical. The width 32 (FIG. 5) of each jaw is equal to or greater than the length 34 (FIG. 5) of the jaw. In particular, the upper jaw 22 and the lower jaw 24 have a semi-circular or "clam-shape" as shown in FIG. 1. The importance of these dimensions and shapes are that upon closure of the upper 22 and lower 24 jaws over the puncture or opening of a wound, the sides of the puncture or opening are totally enclosed within the leak clip 20 (FIG. 13). Therefore, there are no "unenclosed" portions of the puncture or wound that may continue to leak as occurs when a conventional elongated clip clamps only a portion of the puncture or wound. The inside of the upper jaw 22 and the inside of the lower jaw 24 comprise a concave palate 36A and 36B, respectively. These concave palates 36A and 36B provide relief for the sides of the opening/puncture to flow once they are compressed between the jaws 22 and 24.

It should be noted at this juncture, that the teeth 28A and 28B do not have to cover the entire periphery 26A and 26B, respectively; rather, the teeth 28A and 28B can be limited to the front portion of the peripheries 26A and 26B. In either case, the teeth 28A and 28B are interdigitating, i.e., they seat between one another upon closure of the jaws 22 and 24.

Figure 3:
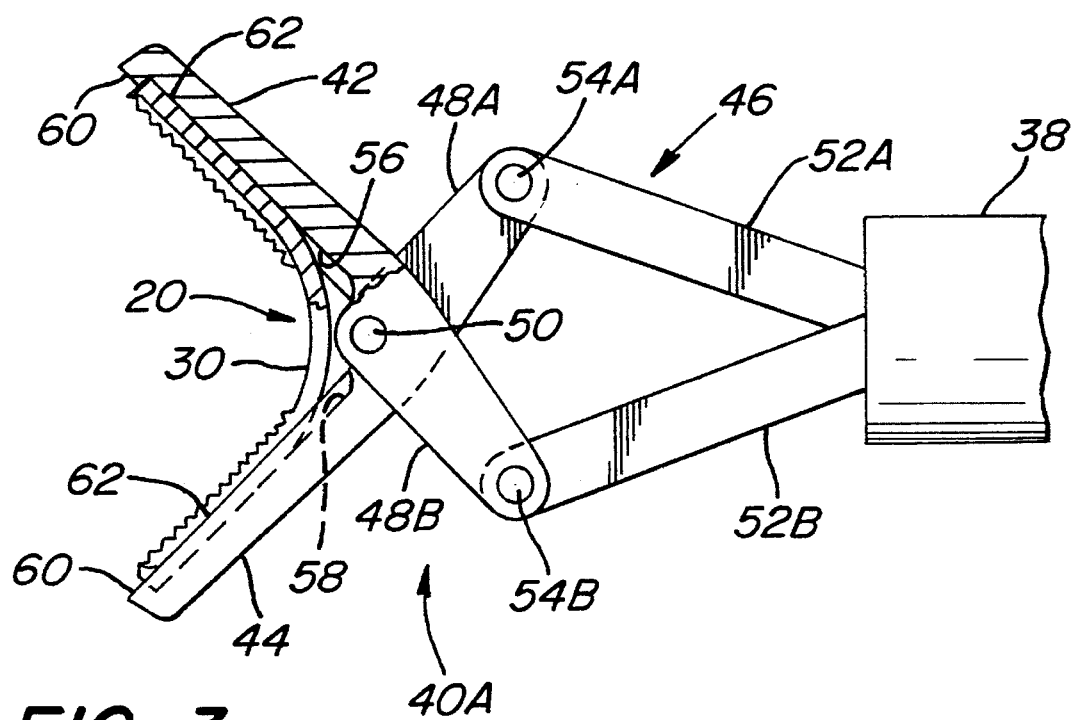
FIG. 3 is a partially broken, side elevation view of the first embodiment of the leak clip installed in an open position within a dual-movable jaws applicator.
Figure 4:
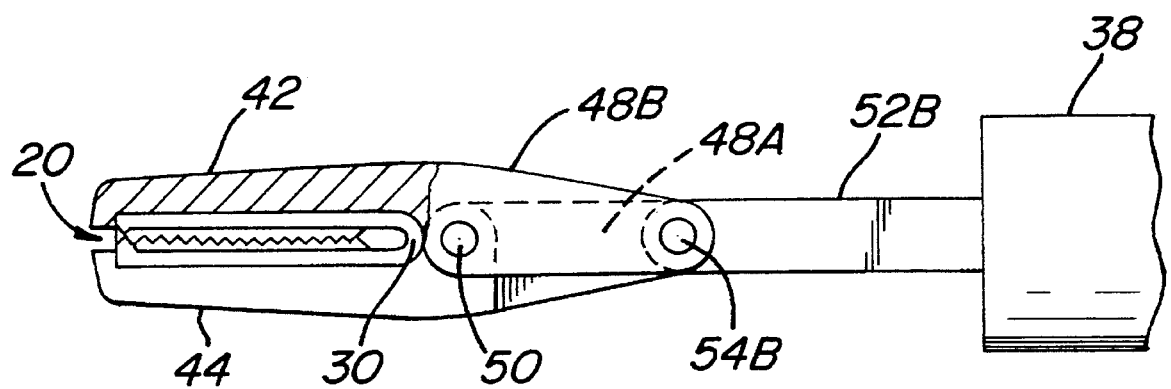
FIG. 4 is a partially broken, side elevation view of the first embodiment of the leak clip of FIG. 3 in a closed position.

The leak clip 20 requires an applicator, the distal end 38 of which is shown in FIGS. 3–4, for applying the leak clip 20 to an internal body organ, e.g., gallbladder, common bile duct, bowel/stomach, large blood vessels. The distal end 38 is insertable through a trocar (not shown) while the proximal end (not shown) of the applicator includes an operator handle portion (also not shown) with which the surgeon grasps and controls the applicator. It should be noted at this juncture that the applicator head 40A (FIGS. 3–5) or 40B (FIGS. 6–8), coupled to the distal end 38 of the applicator, is designed to accommodate the leak clip 20 and is therefore part of the present invention. However, the grasping/controlling operation of the applicator at the proximal end is well-known in the art and is therefore omitted from this patent application.

The first applicator head embodiment 40A comprises an upper jaw receptacle 42 and a lower jaw receptacle 44 driven by a linkage assembly 46. The linkage assembly 46 comprises forward linkages 48A and 48B having corresponding ends that form a fixed pivot to the upper jaw receptacle 42 and the lower jaw receptacle 44, respectively, at a hinge point 50 of the applicator head 40A. The other ends of the forward linkages 48A and 48B are pivotally coupled to driver linkages 52A and 52B, respectively, at hinge points 54A and 54B. The leak clip 20 is force fitted into the upper jaw receptacle 42 and the lower jaw receptacle 44. The force fit is accomplished via a respective recess 56 and 58 in the upper receptacle 42 and the lower receptacle 44 for seating the leak clip 20, as shown in FIGS. 3–4. Each recess has a tip 60 and sidewalls 62 that hold the leak clip 20 within the recesses 56 and 58.

Figure 12:
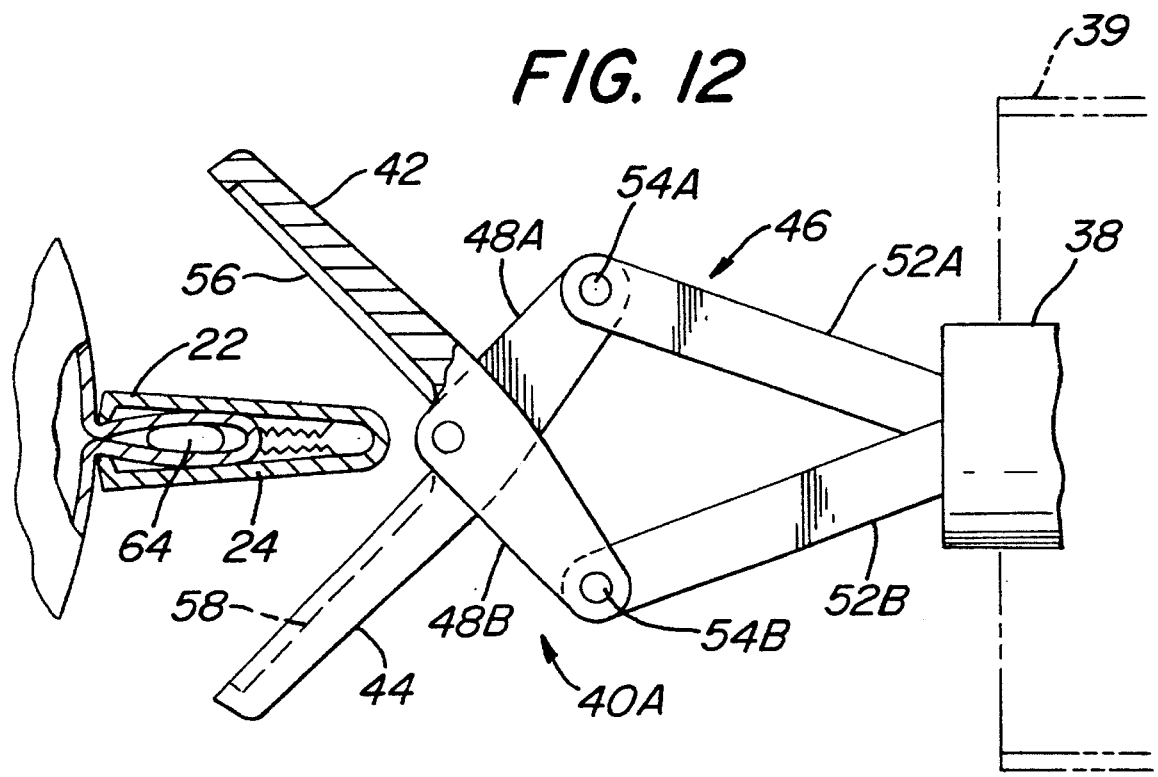
FIG. 12 is a view of a manually-removable leak clip.

Operation of the first applicator head 40A embodiment is as follows: The applicator 38 with the leak clip 20 disposed in the applicator head 40A is fed down through the trocar 39 (FIG. 12). Once the leak clip 20 is adjacent the opening/puncture, the surgeon activates the applicator 38, thereby causing the linkage assembly 46 to compress the upper jaw receptacle 42 and the lower jaw receptacle 44 together (FIG. 4). When the leak clip 20 is applied to an injured organ, this action closes the leak clip 20 over the entire opening/puncture while disengaging the leak clip 20 from the applicator head 40A. As shown clearly in FIG. 12, the leak clip 20 encloses an opening/puncture 64 of an injured organ 66 (e.g., gallbladder, common bile duct, bowel/stomach, large blood vessels) within the upper jaw 22 and the lower jaw 24. The closure of the jaws 22 and 24 pinches the injured organ 66, behind the opening 64, tight enough to prevent any further egress of contaminating fluid from the opening 64. The injured organ 66 can then be removed by the surgeon without the concern for leaking fluids contaminating the surrounding area.

Figure 6:
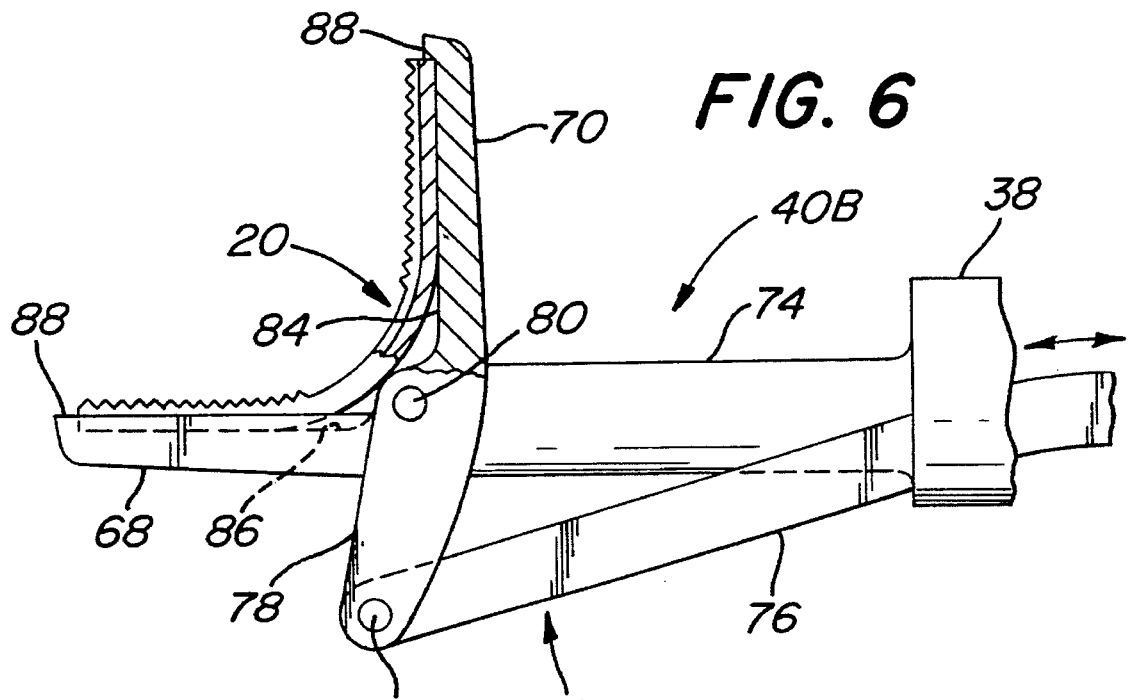
FIG. 6 is a partially broken, side elevation view of the first embodiment of the leak installed in an open position within a single-movable jaw applicator.
Figure 7:
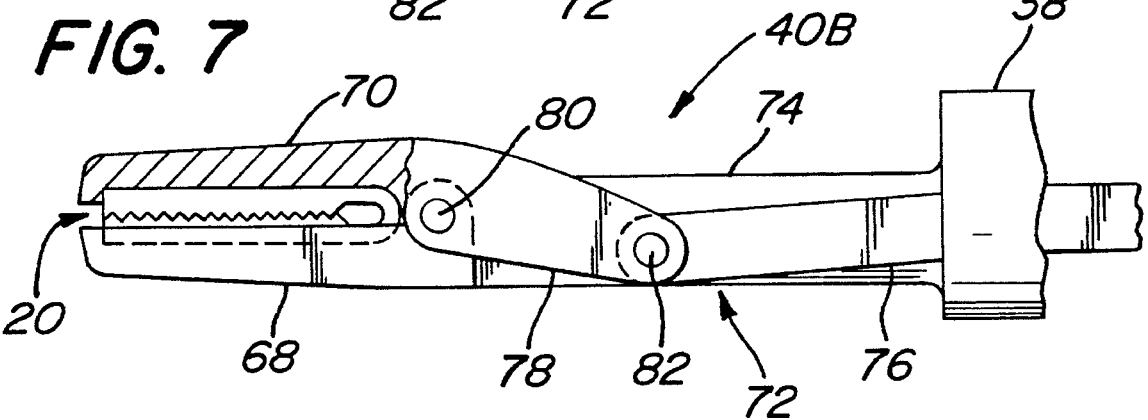
FIG. 7 is a partially broken, side elevation view of the first embodiment of the leak clip of FIG. 6 in a closed position.
Figure 8:
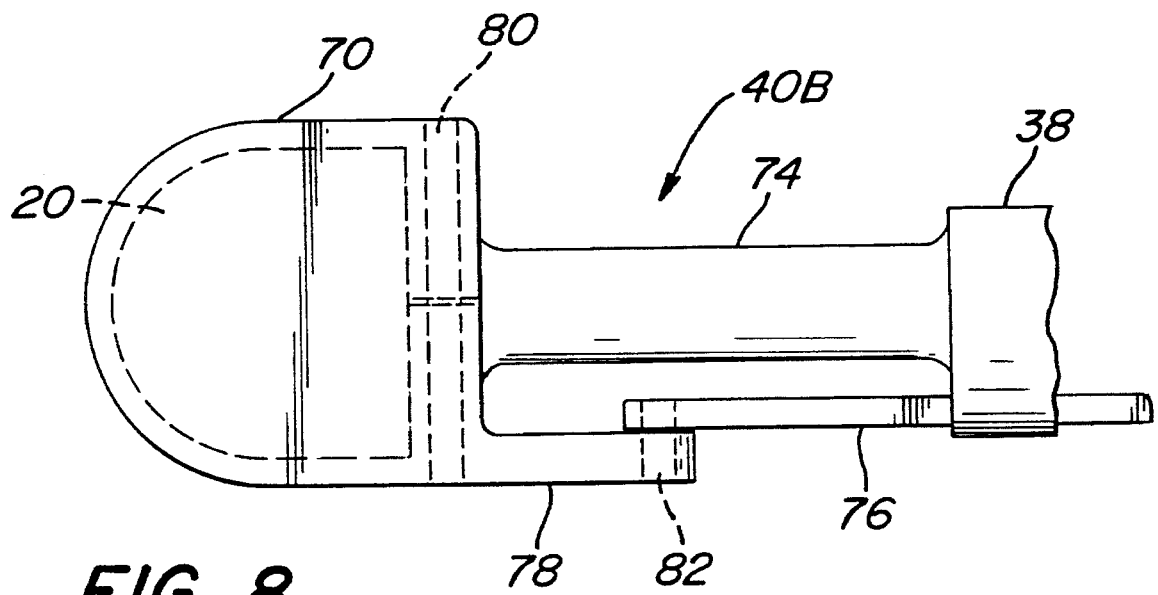
FIG. 8 is a top plan view of FIG. 7.

The second applicator head embodiment 40B comprises a stationary lower jaw 68 and a movable upper jaw receptacle 70 driven by a linkage assembly 72 that permits the application of the leak clip 20 to the puncture/opening in an "L-shaped" orientation, as shown in FIG. 6. The stationary lower jaw receptacle 68 forms the distal end of the applicator shank 74. The linkage assembly 72 comprises a driver arm 76 that rotates a linkage 78 about a fixed pivot point 80. The fixed pivot point 80 is formed between one side of the movable upper jaw receptacle 70 and the applicator shank 74. The driver arm 76 is coupled to the linkage 78 at a translatable pivot point 82. In this case, the leak clip 20 is force fitted into the lower jaw receptacle 68 and the upper jaw receptacle 70. The force fit is accomplished via a respective recess 84 and 86 in the lower receptacle 68 and the upper receptacle 70 for seating the leak clip 20, as shown in FIGS. 6–7. Each recess has a tip 88 and sidewalls 90 that hold the leak clip 20 within the recesses 84 and 86.

Operation of the second applicator head 40B embodiment is as follows: The applicator 38 with the leak clip 20 disposed in the applicator head 40B is fed down through the trocar (not shown) in the "L-shaped" orientation as shown in FIG. 6. Once the leak clip 20 is adjacent the puncture/opening, the surgeon activates the applicator 38 by pulling back on the driver arm 76 in the direction 92 shown in FIG. 7. Movement of the driver arm 76 in the direction 92 causes the translatable pivot point 82 to move in a counterclockwise direction, thereby causing the linkage 78 to also rotate counterclockwise about the fixed pivot point 80. This action causes the movable upper jaw 70 to close against the stationary lower jaw 68, thereby closing the leak clip 20. The surgeon then pushes forward slightly on the driver arm 76 in the direction 93 shown in FIG. 7 to disengage the applicator head 40B from the leak clip 20. It should be noted that the linkage 78 and the driver arm 76 are not horizontally aligned in FIG. 7; this allows the surgeon the ability to push forward on the driver arm 76 in order to accomplish the disengagement of the leak clip 20.

Figure 2:
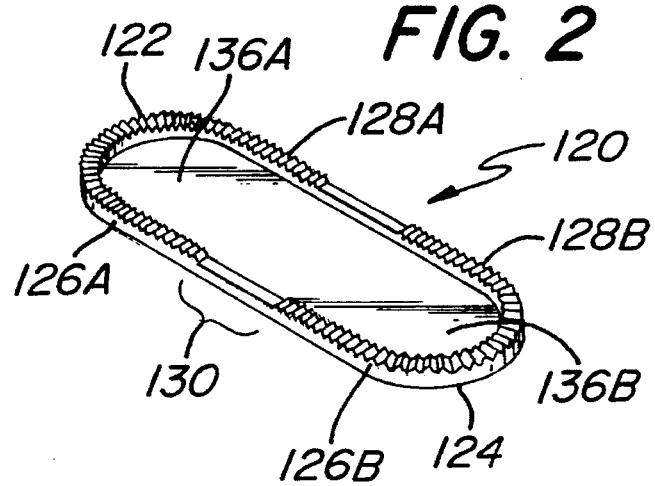
FIG. 2 is an isometric view of a second embodiment of the leak clip.

There is shown in FIG. 2 a second embodiment of a leak clip 120 that comprises an upper jaw 122 and a lower jaw 124 each having opposing outer peripheries 126A and 126B that contain upper teeth 128A and lower teeth 128B. The leak clip 120 is preferably a unitary member that is bent open in a 180° configuration to form the upper jaw 122 and the lower jaw 124. The center of the midportion 130 acts as a hinge for the upper jaw 122 and lower jaw 124. The leak clip 120 comprises a material that permits the bent midportion 130 to maintain jaws 122 and 124 in a closed position (FIG. 10) when these jaws 122 and 124 are brought together by a leak clip applicator, to be discussed later.

The shape of the upper jaw 122 and lower jaw 124 are identical. The width 132 (FIG. 11) of each jaw is equal to or greater than the length 134 (FIG. 11) of the jaw. In particular, the upper jaw 122 and the lower jaw 124 have a semi-circular or "clam-shape" as shown in FIG. 2. The importance of these dimensions and shapes are that upon closure of the upper 122 and lower 124 jaws over the puncture or opening of a wound, the sides of the puncture or opening are totally enclosed within the leak clip 120, as shown with the leak clip 20 in FIG. 13. Therefore, there are no "unenclosed" portions of the puncture or wound that may continue to leak as occurs when a conventional elongated clip clamps only a portion of the puncture or wound. The inside of the upper jaw 122 and the inside of the lower jaw 124 comprise a concave palate 136A and 136B, respectively. These concave palates 136A and 136B provide relief for the sides of the opening/puncture to flow once they are compressed between the jaws 122 and 124.

It should be noted at this juncture, that the teeth 128A and 128B do not have to cover the entire periphery 126A and 126B, respectively; rather, the teeth 128A and 128B can be limited to the front portion of the peripheries 126A and 126B. In either case, the teeth 128A and 128B are interdigitating, i.e., they seat between one another upon closure of the jaws 122 and 124.

As with the leak clip 20, the leak clip 120 requires an applicator, the distal end 138 of which is shown in FIGS. 9–11, for applying the leak clip 120 to an internal body organ, e.g., gallbladder, common bile duct, bowel/stomach, large blood vessels. The distal end 138 is insertable through a trocar (not shown) while the proximal end (not shown) of the applicator includes an operator handle portion (also not shown) with which the surgeon grasps and controls the applicator. It should be noted at this juncture that the applicator head 140 (FIGS. 9–11), coupled to the distal end 138 of the applicator, is designed to accommodate the leak clip 120 and is therefore part of the present invention. However, the grasping/controlling operation of the applicator at the proximal end is well-known in the art and is therefore omitted from this patent application.

The applicator head embodiment 140 comprises a stationary lower jaw receptacle 168 and a movable upper jaw receptacle 170 driven by a linkage assembly 172 that permits the application of the leak clip 120 to the puncture/opening from the 180° configuration, as shown in FIGS. 9 and 11. The stationary lower jaw receptacle 168 forms the distal end of the applicator shank 174. The upper jaw receptacle 170 is disposed within a recess 194 in the applicator shank 174 when the applicator head 140 is in the 180° configuration (FIG. 9). The linkage assembly 172 comprises a "U-shaped" driver frame 176 (FIG. 11) having ends 176A and 176B that are pivotally coupled to respective ends of respective linkages 178A and 178B. A main driver arm 182 simultaneously drives the ends 176A and 176B at the surgeon's control. Each linkage 178A and 178B forms a respective fixed pivot point 180A and 180B between the upper jaw receptacle 170 and the stationary jaw receptacle 168. In this case, the leak clip 120 is force fitted into the stationary lower jaw receptacle 168 and the movable upper jaw receptacle 170. The force fit is accomplished via a respective recess 184 and 186 in the lower jaw receptacle 168 and the upper jaw receptacle 170 for seating the leak clip 120, as shown in FIG. 10. Each recess has a tip 188 and sidewalls that hold the leak clip 120 within the recesses 184 and 186.

Operation of the applicator head 140 embodiment is as follows: The applicator 138 with the leak clip 120 disposed in the applicator head 140 is fed down through the trocar (not shown) in the 180° configuration, as shown in FIG. 9. Once the leak clip 120 is adjacent the puncture/opening, the surgeon activates the applicator 138 by pulling back on the main driver arm 182 in the direction 192 shown in FIG. 9. Movement of the main driver arm 182 in the direction 192 causes the linkages 178A and 178B to move in a counterclockwise direction about the respective fixed pivot points 180A and 180B. Next, the surgeon pushes the main driver arm 182 in the direction 193 shown in FIG. 10. This action causes the movable upper jaw 170 to close against the stationary lower Jaw 168, thereby closing the leak clip 120. The surgeon then pulls back slightly on the main driver arm 182 in the direction 192 to release the leak clip 120 from the applicator head 140 embodiment. The result of applying the leak clip 120 to the opening/puncture of an injured organ is similar to that shown in FIG. 12.

There is shown in FIG. 13 a third embodiment of a leak clip 220 that is similar to the leak clip 20. The only difference is the presence of winglets 296A and 296B that are disposed on the outside of the leak clip 220 surface, on either side of the hinge 230 of the leak clip 220. These winglets 296A and 296B permit the opening/removal of the leak clip 220 from the injured organ 66; the leak clips 20 and 120 can only be removed from the injured organ once the organ is removed from the patient.

Figure 14:
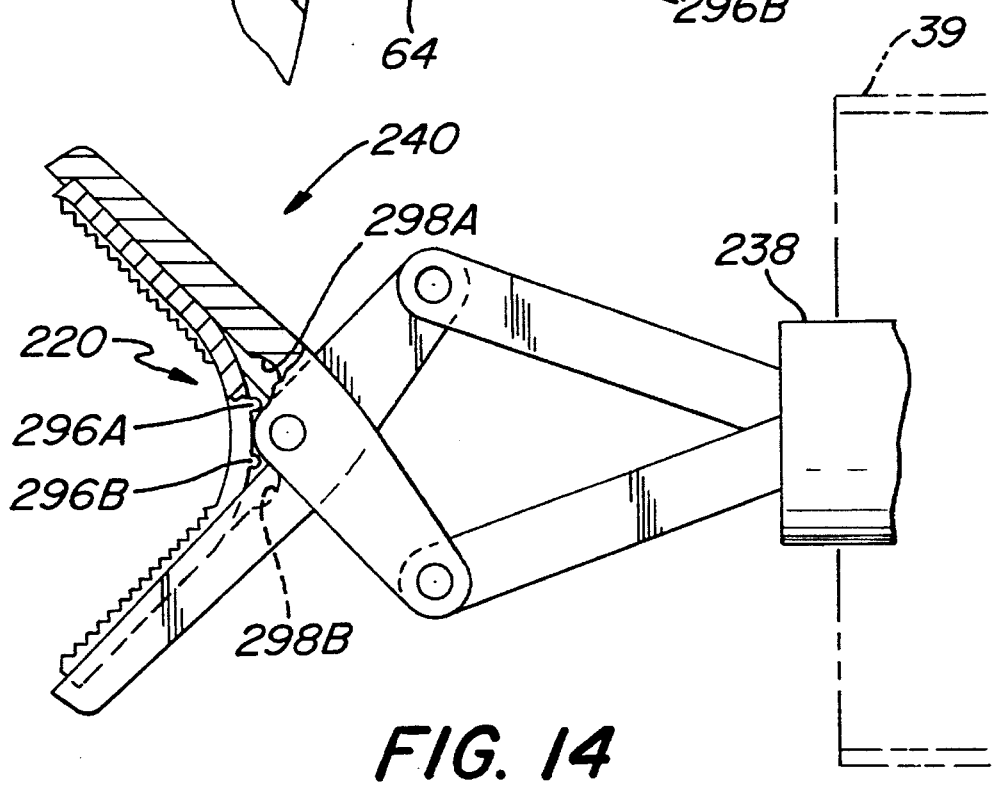
FIG. 14 is a side elevation view of the manually-removable leak clip installed within a corresponding applicator.

As with the leak clip 20, the leak clip 220 requires an applicator, the distal end 238 of which is shown in FIG. 14, for applying the leak clip 220 to an internal body organ, e.g., gallbladder, common bile duct, bowel/stomach, large blood vessels. The distal end 238 is insertable through a trocar 39 while the proximal end (not shown) of the applicator includes an operator handle portion (also not shown) with which the surgeon grasps and controls the applicator. It should be noted at this juncture that that the applicator head 240 (FIG. 14), coupled to the distal end 238 of the applicator, is designed to accommodate the leak clip 220 and is therefore part of the present invention. However, the grasping/controlling operation of the applicator at the proximal end is well-known in the art and is therefore omitted from this patent application.

The applicator head embodiment 240 is similar to the applicator head embodiment 40A described earlier and operates similarly. The only difference in the applicator head embodiment 240 is the presence of two respective openings 298A and 298B for receiving the respective winglets 296A and 296B when the leak clip 220 is force fitted within the applicator head embodiment 240.

Without further elaboration, the foregoing will so fully illustrate my invention that others may, by applying current or future knowledge, readily the same for use under various conditions of service.

I claim:

1. An apparatus for quickly closing an opening in an internal body part to prevent the leakage of contaminating fluids from the opening, said apparatus comprising:

a clamp having a pair of movable jaws pivotally coupled, each of said jaws having a width of a sufficient dimension to encompass the entire opening whenever said jaws are brought into contact with each other;

each of said jaws having a periphery containing teeth, said respective teeth interdigitating whenever said jaws are brought into contact with each other; and applicator means for releasably retaining said clamp for applying said clamp to the opening and then releasing said clamp from said applicator means.

2. The apparatus of claim 1 wherein said periphery contains teeth located only at the front portion of each of said jaws.

3. The apparatus of claim 1 wherein each of said jaws comprises a semi-circular contour and each of said jaws are pivotally joined to each other along the edge opposite said semi-circle.

4. The apparatus of claim 1 wherein said jaws are pre-disposed at a predetermined angular orientation.

5. The apparatus of claim 4 wherein said predetermined angular orientation is given by an "L-shape" formed between said pair of jaws.

6. The apparatus of claim 1 wherein each of said jaws comprises a respective outer surface, each of said respective outer surfaces having a winglet protruding therefrom.

7. The apparatus of claim 4 wherein said predetermined angular orientation is a 180° orientation formed between said pair of jaws.

8. The apparatus of claim 4 wherein said applying means comprises a pair of jaw receptacles that are pre-disposed to each other at said predetermined angular orientation.

9. The apparatus of claim 6 wherein said periphery contains teeth located only at the front portion of each of said jaws.

10. The apparatus of claim 6 wherein each of said jaws comprises a semi-circular contour and each of said jaws are pivotally joined to each other along the edge opposite said semi-circle.

11. The apparatus of claim 6 wherein said jaws are predisposed at a predetermined angular orientation.

12. The apparatus of claim 11 wherein said predetermined angular orientation is given by an "L-shape" formed between said pair of jaws.

13. The apparatus of claim 11 wherein said applying means comprises a pair of jaw receptacles that are pre-disposed to each other at said predetermined angular orientation.

14. The apparatus of claim 13 wherein said applying means is insertable through the trocar at said predetermined angular orientation.

15. The apparatus of claim 14 wherein said jaw receptacles receive respective ones of said pair of jaws, said pair of jaw receptacles having corresponding apertures through which a respective winglet protrudes.

16. The apparatus of claim 15 wherein said applying means is controllable to permit the closing of said pair of jaw receptacles in order to close said pair of jaws entirely about the opening.

17. The apparatus of claim 8 wherein said applying means is insertable through the trocar at said predetermined angular orientation.

18. The apparatus of claim 17 wherein said jaw receptacles receive respective ones of said pair of jaws.

19. The apparatus of claim 18 wherein said applying means is controllable to permit the closing of said pair of jaw receptacles in order to close said pair of jaws entirely about the opening.

20. The apparatus of claim 19 wherein said pair of jaw receptacles comprises an upper movable jaw receptacle and a lower stationary jaw receptacle.

21. An apparatus for quickly closing an opening in an internal body part to prevent the leakage of contaminating fluids from the opening, said apparatus comprising:

a clamp having a pair of movable jaws pivotally coupled, each of said jaws having a width of a sufficient dimension to encompass the entire opening whenever said jaws are brought into contact with each other and wherein said jaws are predisposed at a predetermined angular orientation of 180° formed between said pair of jaws;

each of said jaws having a periphery containing teeth, said respective teeth interdigitating whenever said jaws are brought into contact with each other; and means for applying said clamp to the opening, said clamp being releasably secured within said means for applying and wherein said means for applying is insertable through a trocar.

22. An apparatus for quickly closing an opening in an internal body part to prevent the leakage of contaminating fluids from the opening, said apparatus comprising:

a clamp having a pair of movable jaws pivotally coupled, each of said jaws having a width of a sufficient dimension to encompass the entire opening whenever said jaws are brought into contact with each other and wherein said jaws are predisposed at a predetermined angular orientation;

each of said jaws having a periphery containing teeth, said respective teeth interdigitating whenever said jaws are brought into contact with each other; and means for applying said clamp to the opening, said clamp being releasably secured within said means for applying and wherein said applying means is insertable through a trocar and wherein said applying means comprises a pair of jaw receptacles that are pre-disposed to each other at said predetermined angular orientation.

23. The apparatus of claim 22 wherein said applying means is insertable through the trocar at said predetermined angular orientation.

24. The apparatus of claim 23 wherein said jaw receptacles receive respective ones of said pair of jaws.

25. The apparatus of claim 24 wherein said applying means is controllable to permit the closing of said pair of jaw receptacles in order to close said pair of jaws entirely about the opening.

26. The apparatus of claim 25 wherein said pair of jaw receptacles comprises an upper movable jaw receptacle and a lower stationary jaw receptacle.

27. An apparatus for quickly closing an opening in an internal body part to prevent the leakage of contaminating fluids from the opening, said apparatus comprising:

a clamp having a pair of movable jaws pivotally coupled, each of said jaws having a width of a sufficient dimension to encompass the entire opening whenever said jaws are brought into contact with each other and wherein each of said jaws comprises a respective outer surface, each of said respective outer surfaces having a winglet protruding therefrom;

each of said jaws having a periphery containing teeth, said respective teeth interdigitating whenever said jaws are brought into contact with each other; and means for applying said clamp to the opening, said clamp being releasably secured within said means for applying and wherein said means for applying is insertable through a trocar.

28. The apparatus of claim 27 wherein said periphery contains teeth located only at the front portion of each of said jaws.

29. The apparatus of claim 27 wherein each of said jaws comprises a semi-circular contour and each of said jaws are pivotally joined to each other along the edge opposite said semi-circle.

30. The apparatus of claim 27 wherein said jaws are pre-disposed at a predetermined angular orientation.

31. The apparatus of claim 30 wherein said predetermined angular orientation is given by an "L-shape" formed between said pair of jaws.

32. The apparatus of claim 30 wherein said applying means comprises a pair of jaw receptacles that are pre-disposed to each other at said predetermined angular orientation.

33. The apparatus of claim 32 wherein said applying means is insertable through the trocar at said predetermined angular orientation.

34. The apparatus of claim 33 wherein said jaw receptacles receive respective ones of said pair of jaws, said pair of jaw receptacles having corresponding apertures through which a respective winglet protrudes.

35. The apparatus of claim 34 wherein said applying means is controllable to permit the closing of said pair of jaw receptacles in order to close said pair of jaws entirely about the opening.

* * * * *